United States Patent [19]

Lee et al.

[11] Patent Number: 4,911,718

[45] Date of Patent: Mar. 27, 1990

[54] FUNCTIONAL AND BIOCOMPATIBLE INTERVERTEBRAL DISC SPACER

[75] Inventors: Casey K. Lee, Short Hills; Noshir A. Langrana, Robbinsville; Harold Alexander, Short Hills; Alastair J. Clemow; Elizabeth H. Chen, both of Princeton; John R. Parsons, Perth Amboy, all of N.J.

[73] Assignees: University of Medicine & Dentistry of N.J., Newark; Rutgers University, Piscataway; Johnson & Johnson, New Brunswick, all of N.J.

[21] Appl. No.: 205,076

[22] Filed: Jun. 10, 1988

[51] Int. Cl.[4] .......................... A61F 2/44; A61F 2/30
[52] U.S. Cl. ........................................ 623/17; 623/18
[58] Field of Search ...................... 57/902; 623/11, 13, 623/12, 16, 18, 19, 20, 21, 22, 23

[56] References Cited

U.S. PATENT DOCUMENTS

| | | | |
|---|---|---|---|
| 3,503,199 | 3/1970 | Nesbitt-Dufort | 57/902 |
| 3,867,728 | 2/1975 | Stubstad et al. | 623/13 |
| 4,356,571 | 11/1982 | Esper et al. | 623/11 |
| 4,512,038 | 4/1985 | Alexander et al. | 623/16 |
| 4,711,286 | 12/1987 | Kabe et al. | 57/902 |
| 4,714,467 | 12/1987 | Lechner et al. | 623/16 |

FOREIGN PATENT DOCUMENTS 0030583  6/1981  European Pat. Off. ............ 623/160

Primary Examiner—Richard J. Apley
Assistant Examiner—David J. Isabella
Attorney, Agent, or Firm—Klauber & Jackson

[57] ABSTRACT

The construction and manufacturing technique for a functional biocompatible intervertebral disc spacer is described. This device is useful for a replacement for a degenerated disc in certain treatments of back pain and spinal disease. The disc spacer possesses mechanical properties akin to those of the normal disc and will preserve normal functions of the spinal motion segment. The device achieves the desired properties by providing reinforcing fibers of appropriate orientation and number within an elastomeric matrix.

29 Claims, 6 Drawing Sheets

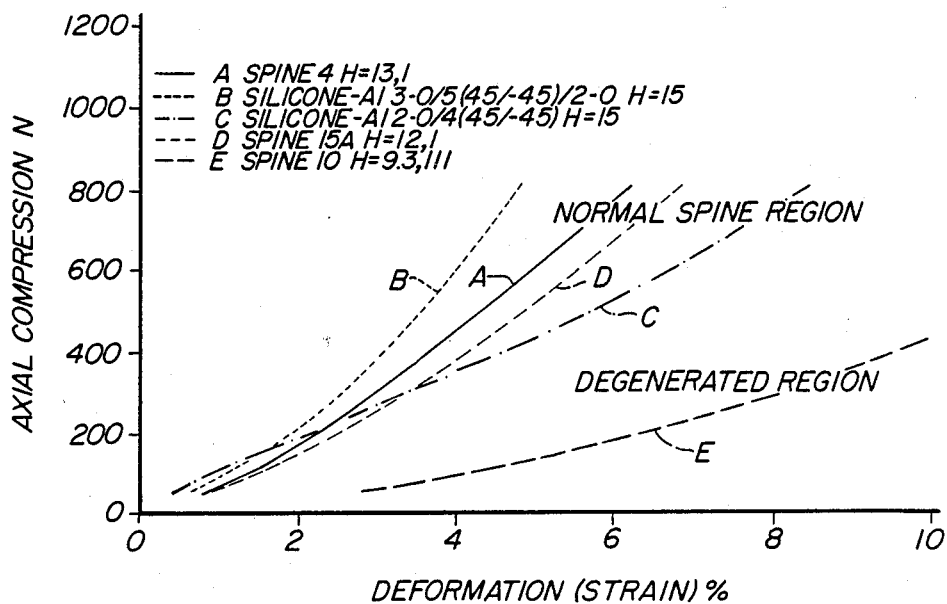
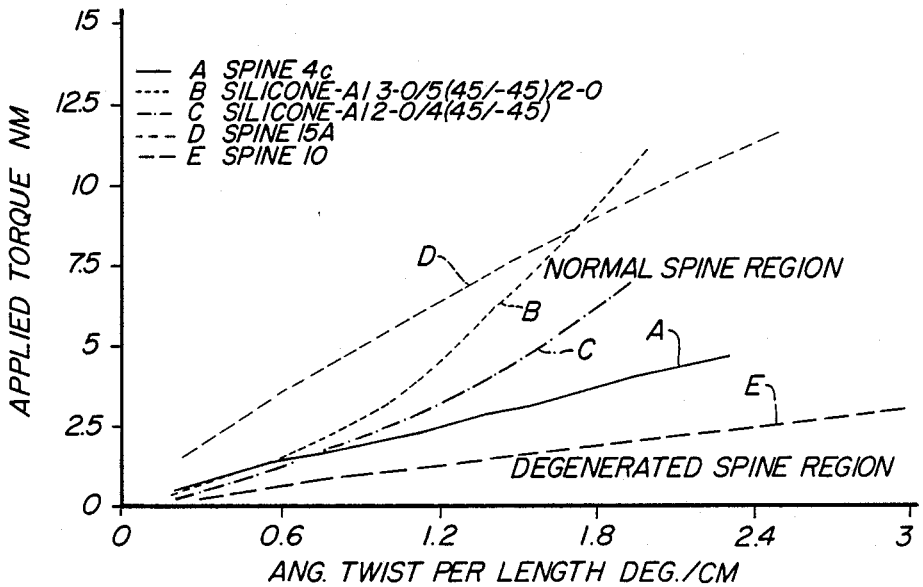

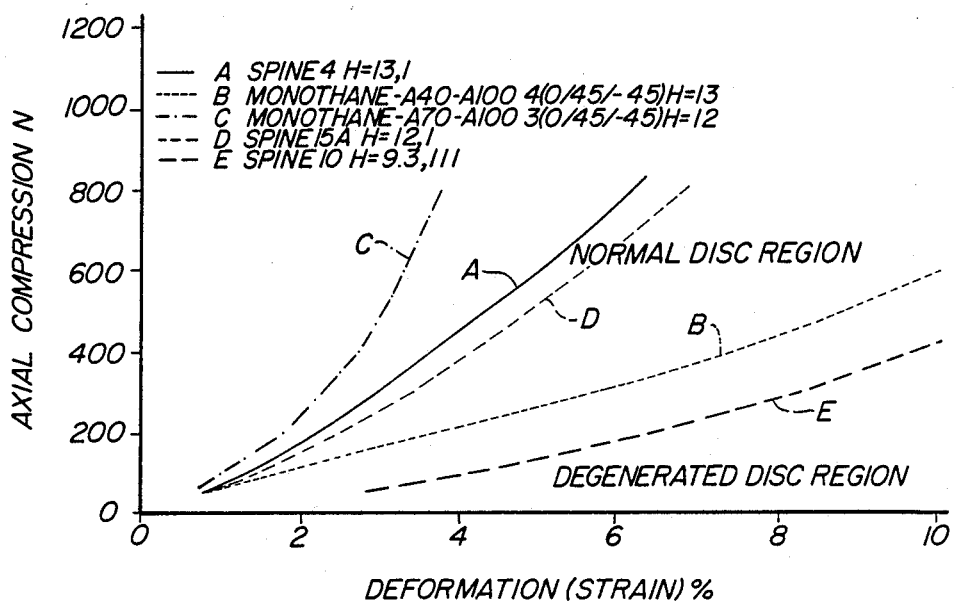
FIG-8 COMPRESSION TEST
NATURAL DISCS VS. POLYURETHANE SPACERS
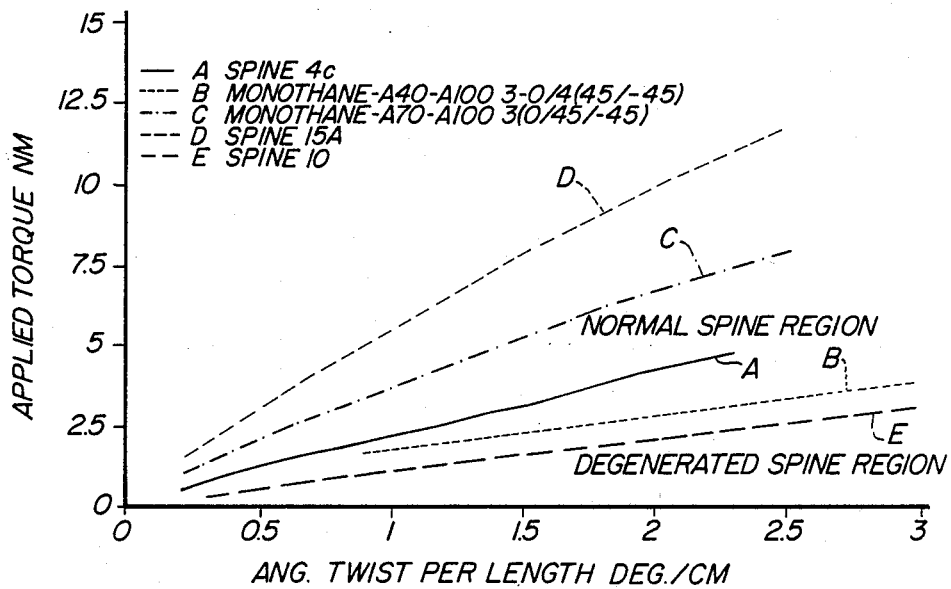
FIG-9 TORSION TEST WITH 800N AXIAL COMPRESSION
NATURAL SPINE VS. POLYURETHANE SPACERS

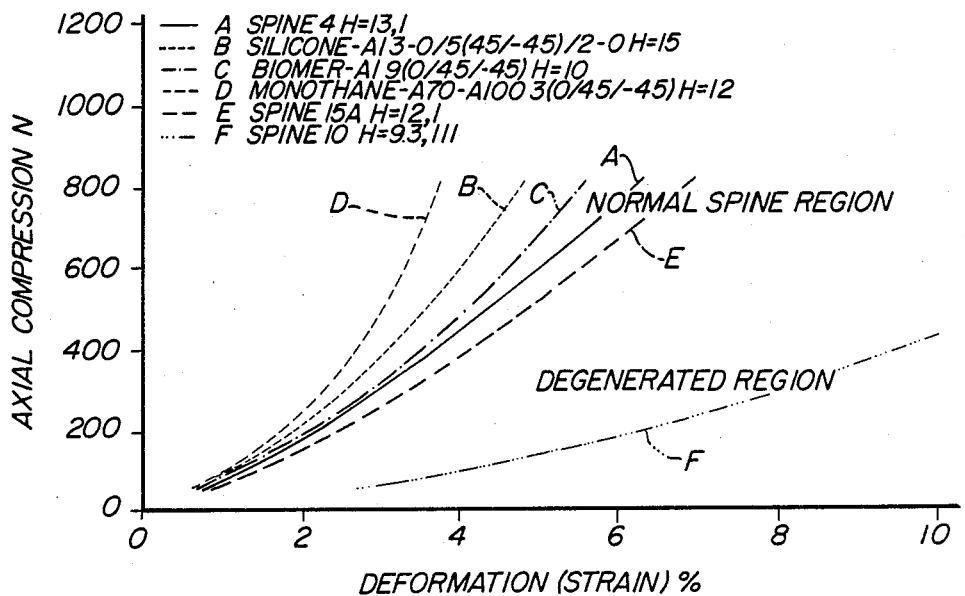
FIG-10 COMPRESSION TEST NATURAL SPINE VS. DISC SPACER
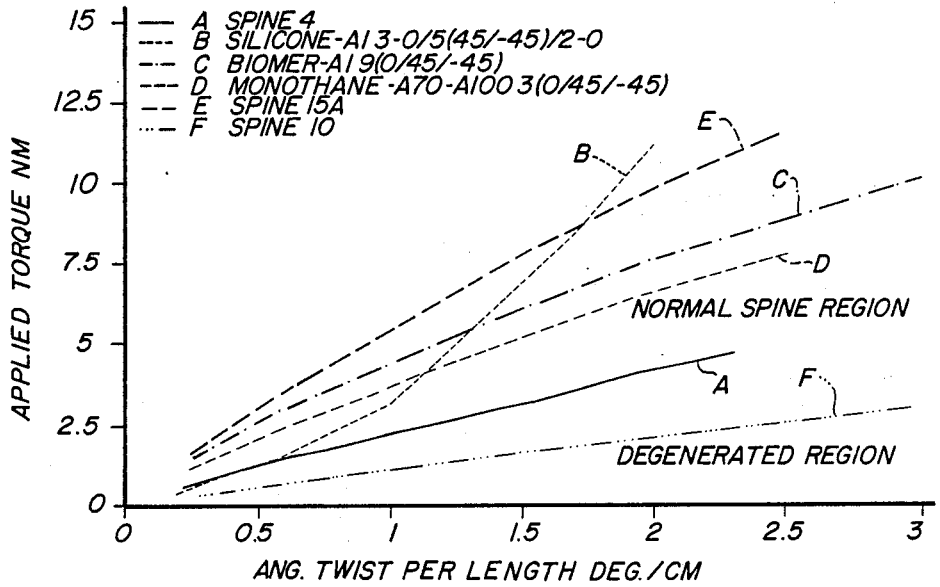
FIG-11 TORSION TEST WITH 800N AXIAL COMPRESSION NATURAL SPINE VS. DISC SPACER

FUNCTIONAL AND BIOCOMPATIBLE INTERVERTEBRAL DISC SPACER

BACKGROUND OF THE INVENTION

The intervertebral disc is a complex joint anatomically and functionally. It is composed of three component structures: the nucleus pulposus, the annulus fibrosus and the vertebral endplates. The biomedical composition and anatomical arrangements within these component structures are related to the biomechanical function of the disc.

The nucleus pulposus occupies 25-40 percent of the total disc cross-sectional area. It is composed mainly of mucoid material containing mainly proteoglycans with a small amount of collagen. Due to these constituents, the nucleus pulposus has the capacity to bind water and usually contains 70-90 percent water by weight. Because of this high water content, the nucleus may be mechanically described as an incompressible hydrostatic material. The disc is under constant compressive forces even when the spine is not weight bearing as a result of the tension applied by the annulus fibrosus and the intervertebral ligaments.

The annulus fibrosus is a concentrically laminated structure which contains highly aligned collagen fibers and fibrocartilage embedded in amorphous ground substance. The annular layers are oriented at ±30 degrees to the longitudinal axis of the spine. In the inner laminae, these annular layers are anchored to the cartilainous endplate while the outermost layer is attached directly into the osseous tissue of the vertebral body. Usually, the annulus fibrosus has approximately 8-12 layers and has an anterior portion which is about 1.2-1.5 times thicker than its posterior region. Mechanically, the annulus fibrosus is the main stabilizing structure which resists torsional and bending forces applied to the disc. A normal isolated disc provides approximately 35 percent of the torsional rigidity of a whole intervertebral joint.

The two vertebral endplates are composed of hyaline cartilage and separates the disc from the adjacent vertebral bodies. This layer acts as a transitional zone between the hard, bony vertebral bodies and the softer disc.

The spinal disc may be displaced or damaged due to trauma or a disease process. If this occurs, the nucleus pulposus may herniate and protrude into the vertebral canal or intervertebral foramen, in which case, it is known as a herniated or "slipped" disc. This disc may in turn press upon the spinal nerve, that exits the vertebral canal through the partially obstructed foramen, causing pain or paralysis in the area of its distribution. The most frequent site of occurrence of a herniated disc is in the lower lumbar region. A disc herniation in this area often involves the inferior extremities by compressing the sciatic nerve. To alleviate this condition, it may be necessary to remove the involved disc surgically and fuse the two adjacent vertebrae. A number of procedures have been identified and are described in the orthopaedic literature. One such is described in "Orthopedics-Principles and Their Application", Samuel L. Turek, M. D., Lippincott Company, Third Edition, pp. 761-763. In this procedure, a hole is drilled in the spinal column straddling the damaged disc space and the two adjacent vertebral bodies. The hole is then filled with a cylindrical plug or dowel in order to fuse the vertebrae together. The fusion procedure is an excellent method of eliminating symptoms and yet maintaining joint stability, but at the expense of total loss of motion of the fused vertebral joint. The adjacent discs will have increased motion and stress due to the increased majority of the fused segment. In the long term, this change in mechanics of the motion of the spine causes these adjacent discs to degenerate. Obviously, a more desirable situation would involve replacing the damaged disc with a suitable biofunctional equivalent so as to return the patient's spine to normalcy. Heretofore, the development of a prosthetic joint device to replace the injured intervertebral disc has been unsuccessful du to the complexity of the structure and biomechanics of the normal disc.

Other spacers for spinal repair have been developed, see for instance those of U.S. Pat. No. 3,867,728, U.S. Pat. No. 4,309,777, U.S. Pat. No. 4,349,921 and U.S. Pat. No. 4,553,273. None of these, however, have been commercially developed. U.S. Pat. Nos. 4,349,921 and 4,553,273 are essentially rigid bodies which serve to stabilize the spine but do not allow motion within the disc itself. U.S. Pat. No. 4,309,777 consists of a disc which allows motion, but this is achieved by the use of springs contained within the body of the disc.

U.S. Pat. No. 3,867,728 by Stubstad et al. discloses a device which replaces the natural disc with one of similar shape and strength. The disc may be constructed from an elastic polymer such as silicone and reinforced with fabric. The top and bottom surfaces may be provided with an open pored material such as a velour to encourage tissue in growth. The purpose of this invention is to provide a system capable of withstanding the loads imposed upon it during normal human activities. As a result, the preferred construction of the disc provides for reinforcement against only compressional loads. In practice, the spine is subjected to both compressional and torsional loading and, to be successful, any device must be capable of withstanding both forms. In addition to strength, any prosthetic disc must deform elastically in a similar manner to the natural structure in order that normal stresses are induced within the adjacent vertebral bodies. If too stiff a structure is used, then the disc will deform too little, and the natural discs both superior and inferior to the prosthetic device will be required to deform excessively. This is a similar situation to that which occurs when bony fusion across the disc is employed. If, on the other hand, the device possesses too little stiffness, either in compression or torsion, then excessive motion will occur, the device will bulge out and pain may result. This is an equivalent situation to a failed bony fusion. U.S. Pat. No. 3,867,728 describes a device which is concerned only with the ultimate strength and not with any elastic properties. Therefore, the reinforcement of the elastomer through a fabric layer results only in an increase in compressional strength and fails to address the equally important problem of elasticity in compression and torsion.

OBJECTS OF THE INVENTION

It is the object of the present invention to provide a novel intervertebral disc spacer which can be used to replace a damaged or diseased disc with a device that is both strong and elastically comparable to the natural structure.

It is a further object of this invention to provide a novel method of manufacturing a functional and biocompatible intervertebral disc spacer having similar or equivalent biomechanical properties to those of a normal disc.

It is a still further object of the present invention to provide a novel method of alleviating the pain and/or paralysis of a damaged or diseased disc which comprises replacing the damaged or diseased disc with a functional and biocompatible intervertebral disc spacer.

SUMMARY OF THE INVENTION

The present invention relates to a novel functional and biocompatible intervertebral disc spacer, its method of manufacture, and methods of use therefor. More particularly, the present invention concerns a functional and biocompatible intervertebral disc spacer having biomechanical properties similar or equivalent to those of a normal disc.

BRIEF DESCRIPTION OF THE DRAWINGS

FIG. 6 is a graph showing the results of the mechanical behavior of silicone-dacron spacers in the axial compression test.

FIG. 7 is a graph showing the results ff the mechanical behavior of silicone-dacron spacers in the compression torsion test.

FIG. 8 is a graph showing the results of the mechanical behavior of polyurethane-dacron spacers in the axial compression test.

FIG. 9 is a graph showing the results of the mechanical behavior of polyurethane-dacron spacers in the compression torsion test.

FIG. 10 is a graph showing the results of the mechanical behavior of natural disc and spacers in the axial compression test.

FIG. 11 is a graph showing the results of the mechanical behavior of natural disc and spacers in the compression torsion test.

DETAILED DESCRIPTION OF THE INVENTION

Figure 1:
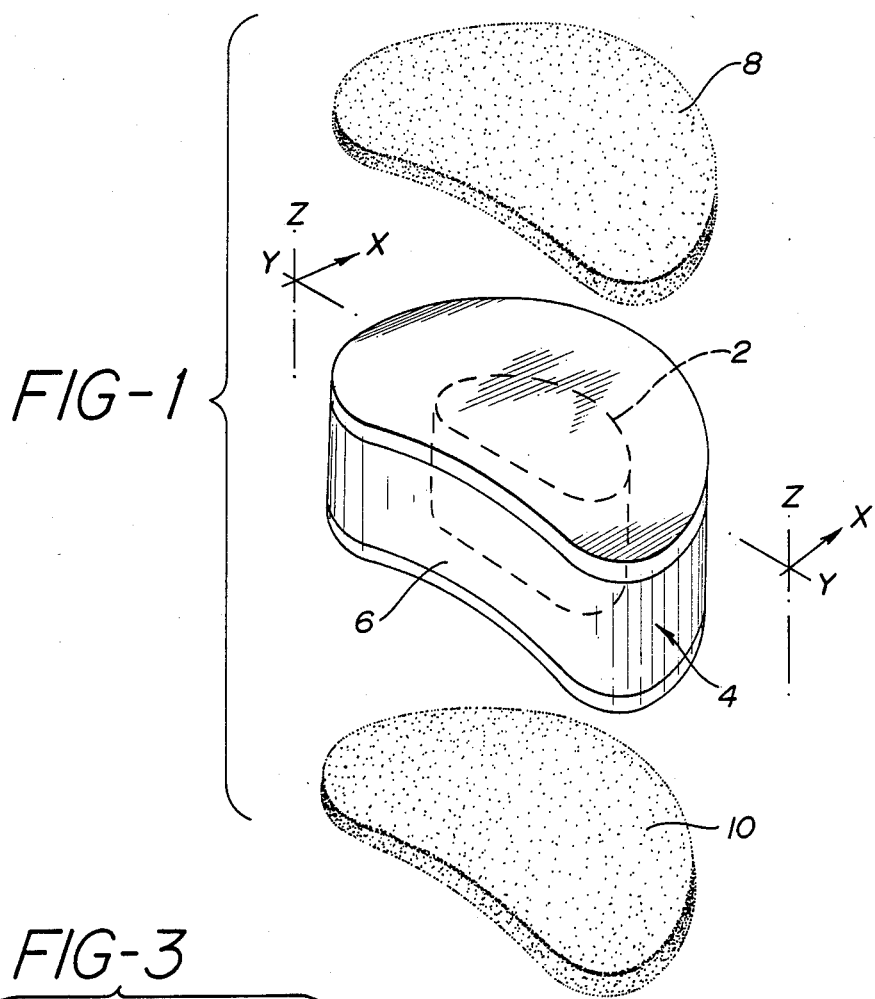
FIG. 1 is a view in perspective of a spinal disc spacer manufactured according to the present invention.

The functional and biocompatible intervertebral spacer of the present invention comprises a central core 2 of biocompatible elastomer shaped so as to approximate the nucleus pulposus of a natural intervertebral disc; laminae 4 wrapping said central core comprised of strips of sheets of reinforcing fiber embedded in a biocompatible elastomer; said laminae being bound together by biocompatible elastomer, and wrapped to sufficient thickness so as to approximate the shape of a natural intervertebral spacer; said laminae arranged in layered structure having specific fiber orientations and having 3-24 laminae; and endplates 8 and 10 comprised f a suitably stiff biocompatible material and affixed, one to each end, to the laminae/central core.

The selection of the number of laminae and the orientation of the fibers in the laminae is accomplished so that the resulting spacer has the approximate mechanical behavior of the natural disc it is designed to replace. Certain combinations of orientations in the fibers of the laminae are preferable. The spacer preferably contains 6-15 laminae, said laminae being applied in patterns of particular fiber orientation.

The biocompatible elastomer utilized in the present invention may be any suitable biocompatible elastomer. Preferred elastomers are thermoset elastomers and thermoplastic elastomers. Suitable thermoset elastomers are those such as silicones and polyurethanes. Suitable thermoplastic elastomers are polyurethanes and thermoplastic silicones. Examples of such biocompatible polyurethane materials are those available as Ethicon Biomer®, a segmented polyether polyurethane which is fabricate into devices by solution casting techniques (Ethicon Inc., Somerville, N.J.). Other polyurethane materials exhibiting appropriate mechanical properties include Conathane< TU400 (Conap Inc., Olean, N.Y.) and Monothane A40, A50 and A70 (Synair Corp., Chattanooga, Tenn.).

The Conathane® polyurethane elastomer is two-part, non-TDI liquid polyurethane casting system. The two components should be mixed thoroughly in plastic or glass containers using plastic or glass stirrers. For example, D PEN®-8488 product is made by mixing equal parts of A and B, whereas TU400 is made by mixing one part of A to 0.867 parts of B. On the other hand Ethicon Biomer® and Monothane® resins are single compound systems and therefore ready to use. The cure time and coating thickness differs for each type of material. For instance, Conathane® products have no restrictions for coating thickness in each layer and take about 20 hours to completely cure. For Ethicon Biomer®, a 2 mm thickness at each coating is permissible while a longer time period and higher temperature is needed for curing. Monothane® resins have to be preheated in order to minimize viscosity. Since the polyurethane elastomers release an isocyanate vapor throughout the curing process, the work is necessarily conducted in well ventilated areas with protective clothing, safety glasses, gloves and a mask.

The reinforcing fiber utilized in the laminae can also be any of a number of suitable reinforcing fibers possessing a combination of high strength and stiffness. Potential fibers include polyethylene (Spectra®), polyester (Dacron®) or polyaramid (Kevlar®, E. I. Dupont DeNemours) fibers, or carbon or glass fibers. For the purposes of this invention, polyester fiber, such as that available as Dacron® Type 56 from Dupont, is preferred.

The reinforcing fiber is embedded in a sheet of the polyurethane elastomer by first wrapping the fiber on thread guides and casting the polyurethane elastomer on the sheets of fiber. After curing, the sheets of fiber are then cut into strips to be utilized to form the laminae of the disc spacer.

Figure 3:
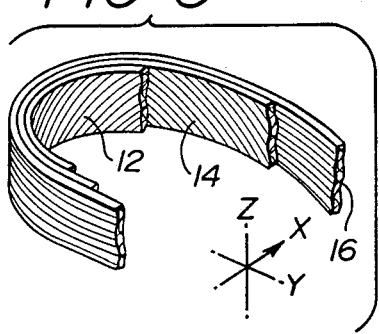
FIG. 3 is a cutaway view showing the laminae having the polymer fibers in the various orientations.
Figure 2:
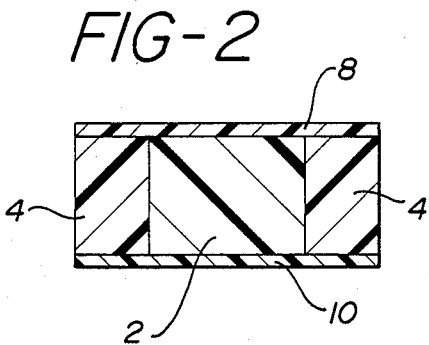
FIG. 2 is a planar view of a disc spacer manufactured according to the present invention.
Figure 4:
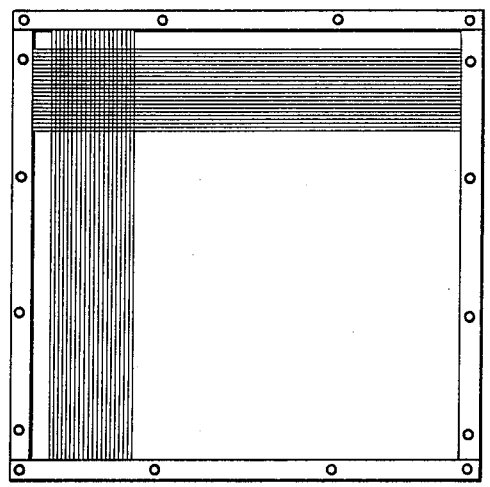
FIGS. 4 and 5 are views of the sheets having thread guides for wrapping the polymer fiber so as to provide laminae having the desired fiber orientation.
Figure 5:
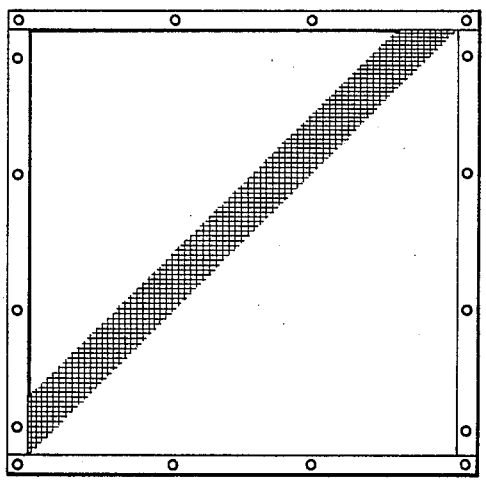
Figure 12:
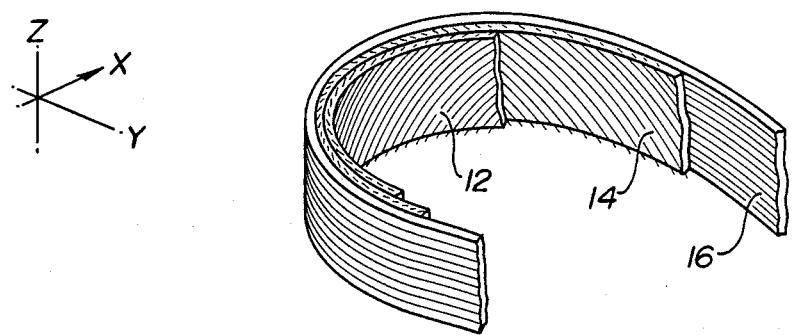
FIG. 12 is a cutaway view of a spacer showing the laminae with protruding polymer fibers.

The laminae 4 of the disc spacer are formed from strips wherein the orientation of the fibers differ. Preferably, some laminae are formed from strips where the polymer fibers are oriented at 0 degrees and some laminae are formed from strips where the polymer fibers are oriented at from 20 to about 50 degrees, either plus or minus, with ±45 degrees being preferred. FIG. 4 and 5 illustrate sheets having thread guides for wrapping the polymer fibers so as to provide laminae having the desired 0 degree and 45 degree fiber orientation. Other fiber orientations may be used depending on the actual mechanical properties of constituent materials and on tee desired final properties of the disc spacer. For the purposes of this invention, the 0 degree orientation refers to the direction along the long axis of the strips. See FIG. 3.

After the sheets of fiber embedded elastomers are formed, they are cut into strips of a suitable width, i.e., preferably about 5-10 mm wide, so as to be utilized to form the laminae. Each spacer contains 3-24 laminae, arranged in layers. The strips of laminae 4 can be formed with or without protruding fibers. The optional feature of these protruding fibers provides additional torsional strength by coupling with the endplates in a spacer of this invention.

The formation of the strips of laminae with protruding fibers is accomplished by forming the net of reinforcing fibers on the thread guides and then covering portions of the net with an elastomer-resistant tape prior to the step of coating the fibers with elastomer. After the sheet of fibers is coated with elastomer and cut into strips, the tape is removed to leave uncoated fibers protruding from each strip.

For the polyurethane spacer, a disc-shaped mold may be utilized to form the laminae around the appropriate core shape. The laminae are wrapped around the core-shaped mold. Multiple laminae may be wrapped about the mold with an appropriate coupling resin between layers. Such a lay-up forms the fiber-reinforced annulus. Upon removal of the mold, the annulus is placed in a cavity mold and resin added to fill the central area. The entire structure is then cured to form the final bonded structure.

The endplates 8 and 10 for use in the spacer of the present invention can be manufactured form a variety of biocompatible materials. The endplates may also incorporate mechanism for attachment to adjacent bony vertebral bodies. Such mechanisms include, but are not limited to, mechanical interlock, frictional fit, in growth into a porous structure such as a porous sintered surface hydroxyapatite coatings or cementing agents such as polymethyl methylacrylate "bone cement." Typically, they are formed from substances such as a biocompatible metal, for instance, precut titanium discs or formed in a mold from polyurethane elastomer or other similar resins. Other metals having similar mechanical properties, e.g. aluminum, can also be utilized. These resins can contain additives such as hydroxyapatite which additionally contribute to their biochemical properties as well as provide a mechanism of bonding of the adjacent bony vertebral bodies to the spacer. When metal endplates are utilized, they are sized so as to approximate the natural vertebral endplate since their function in the spacer is to simulate the vertebral endplate as well as contribute to the overall structural strength of the spacer. Metal endplates may have a porous surface for bone ingrowth stabilization or polymethyl methylacrylate bone cement fixation.

The novel method of manufacture of the spacer of the present invention involves three separate steps; the first being the preparation of the lamina strips for us in the spacer; and the second being the fabrication of the endplates; and the third being actual assembly of the spacer itself. This assembly can be accomplished in a variety of ways depending primarily on the nature of the constituent materials, e.g., thermoset resins or thermoplastics.

The actual formation of the lamina strip is dependent upon the particular reinforcing fiber and elastomer being utilized. If a thermoset resin is utilized, the mixing and curing of each individual elastomer is typically accomplished according to the manufacturer's directions for use of the particular elastomer. It is envisioned that thermoplastic elastomers may also be used in which case molding under heat and pressure according to the manufacturer's directions may be used to fabricate said laminae strip. Typical molding or casting techniques can be used to form polymer endplates. Metallurgical techniques can be used to form metal endplates. Both metal endplates and polymer endplates may have porous surfaces or hydroxyapatite surfaces to aid in attachment to adjacent bony vertebral bodies.

The assembly of the space typically begins with the formation of a suitably shaped and sized core formed of the elastomeric material. See FIG. 1. A metal mold is utilized to form the core 2, to which, after removal from the mold, the strips of laminae 4 are applied circumferentially to a desired thickness. The sides of the disc may then optionally be coated with additional elastomer 6 and the entire structure bonded or cured under heat and pressure in an appropriate sized cavity mold. Finally, the endplates 8 and 10 are applied with additional elastomer to the top and bottom of the disc. Alternately, the endplates may be applied during the bonding/curing process.

Typically, molds are utilized to manufacture spacers having a geometry consistent with that of a natural disc. Suitable molds can be made from aluminum. Although the disc size can, of course, be varied, a suitable size for the spacer is one having a cross section area of 1100 $mm^2$, a major diameter of 44 mm and a minor diameter of 30 mm.

The present invention contemplates manufacture of the spacers in a variety of sizes since one size is not suitable for all people. Additionally, the spacer of the present invention can be sized so that its total diameter is smaller than that of a natural disc, i.e., a size which approximates 30-80% of the diameter of the natural disc. This size o spacer can then be utilized by a physician in cases where only a central part of the natural disc is removed and replaced. In such cases, the damaged or diseased central portion is replaced by a spacer of approximately the same size as the portion removed. This type of replacement is particularly advantageous since the healthy portion of a patient's disc is retained. Obviously, molds can be developed for the various sizes necessary, and it is envisioned that the disc spacer of this invention will be manufactured in a variety of sizes so as to make the necessary selection available to the treating physician.

In this invention, we have found that certain configurations of the lamina strips within the spacer contribute to the enhancement of its mechanical properties. Thus, it is preferable to apply the laminae to the core according to certain "patterns". A preferred method utilizes a pattern of a −45 degree fiber strip 12 as the inner lamina, followed by a +45 degree fiber strip, 14, followed by a 0 degree fiber strip 16. See FIG. 3. This −45/+45/0 degree orientation is continued until 2-5 sets of the −45/+45/0 pattern are applied (a total of 6-15 laminae). Particularly preferred spacers each contain 3-5 sets of the −45/+45/0 degree laminae.

For instance, a disc spacer utilizing Biomer ® as the elastomer, aluminum endplates, and having a wrapping configuration of 3 layers each of 0, +45, −45 degree fiber strips has been found to possess similar properties to that of a natural spinal disc in compression and torsion testing.

The disc spacer of the present invention thus provides a novel method of alleviating the pain and paralysis of a damaged or disease spine which comprises surgically replacing the damaged or diseased natural disc with one manufactured according to the present invention. Depending upon the patient's age and the position of the diseased or damaged disc, a physician will select a suitably sized replacement disc for insertion between the natural vertebrae.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

EXAMPLE 1

Preparation of Thermoset Elastomer-Fiber Laminae (Steps A-D)

A. Preparation of 0 and 45 degree fiber sheets

The reinforcing fibers are wrapped around a square mandrel as shown in FIG. 4 and 5. The number of fiber wraps should correspond to the intended construction of the annular layer. When exposed fibers are desired, the surface of the wired sheet is taped with suitable adhesive tape.

B. Preparation of Coating Elastomer

1. Silastic

The silastic elastomer of choice, i.e., MDX-4-4210 is mixed according to manufacturer's instructions with care being taken to ensure that no entrapped air is present in the final polymer.

2. Conathane®

The two components are mixed according to manufacture's instruction. For example, for TU400, 100 parts of A are mixed with 100 parts B by weight. The two are mixed thoroughly and then the mixture is degassed to remove entrapped air.

3. Biomer®

Biomer is provided in a solution of dimethyl acetamide which is evaporated off to produce the final product. In order to achieve good resultant mechanical properties, care is required at this step to ensure the absence of any water vapor.

4. Monothane®

Articles may be produced from Monothane by heating the resin to a suitable temperature. For 50A hardness material, this is 70° C. for 20 minutes. Different grades of Monothane require different temperatures and time.

C. Formulation of 0, +45/−45 Lamina Strip

The amount of resin used is about 60 mls for making an 11 inch square plate of 1/32 inch thick lamina layer. The manufacturing processes for 0, +45/−45, and 0/+45/−45 degree laminae are similar for each different material.

D. Coating the Prewired Fiber Sheet

Pour a coating of the semi-deaired resin on top of the prewired fiber sheet and cure according to specification of the manufacturer, a process that varies from material to material.

1. Silicone (MDX 4-4210 Silastic)

Cure at 60 to 80 degrees C for 20 to 30 minutes. Full curing is accomplished in three days at room temperature. Cut the finished sheet into 7 to 8 mm strips, with a scalpel, parallel with fibers for 0 degree lamina, and along the centerline of the end tape for 45 degrees lamina. Coat one side of the 0 and +45/−45 degrees laminae with Medical Adhesive Silicone Type A. Apply enough pressure on top of the sandwich strip to secure it in place without squeezing out the bonding glue. Cure at 60 to 80 degrees C for 30 minutes. Twenty-four hours are required for complete vulcanization.

2. Conathane® (TU400)

Heat at 80 degrees C in a nitrogen environment for 4 hours and continue to cure at room temperature for 16 hours. Cut the cured fiber-elastomer composite sheet in a diagonal direction with spacing of 7 mm to form a +45/−45 lamina. For a 0 degree lamina cut parallel to the fiber direction. To make a 0/+45/−45 lamina, coat one side of a 0 degree lamina sheet and one side of +45/−45 strips with a 0.4 mm layer of fresh deaired polyurethane. Then align the +45/−45 degree laminae on top of the 0 degree sheet. Apply enough pressure on top of the strip to hold it, but avoid squeezing out the polyurethane. Cure the 0/+45/−45 sheet in the nitrogen oven as before. Cut along the junction line to form 0/+45/−45 lamina strips.

3. Monothane® (A100)

Heat prewired fiber plate in oven at 135 degrees C for one hour and warm Monothane resins to 70 degrees C for 20 minutes. The preheating time and temperature vary slightly for monothanes of different hardnesses. Pour 60 mls of liquid resin onto the preheated plate. Then cure in an oven at 135 degrees C for 1 hour. Minimum viscosity is obtained between 110 and 115 degrees C. Cut 45 degree strips, 7 mm wide from one side of the plate. The other side still has dacron fibers running along the X and Y axes. Remove one side of fibers form the other side of the plate to prepare radial fiber lamina. Unscrew the borders and place the sheet of radial fibers on the other side. For 0/+45/−45 lamina, pour 60 mls of preheated resin onto fiber sheet, then place in oven at 135 degrees C for 20 min. Remove the plate from the oven and place all 7 mm +45/−45 strips on top of the plate. The +45/−45 laminae should be placed parallel to the X or Y axis of the plate. Cure the 0/+45/−45 plate in the oven at 135 degrees C for 1 hour and 15 min. Finally, cut 7 mm strips of 0/+45/−45 lamina. Each cut should be parallel with the axis.

EXAMPLE 2

Formation of a Spacer with Protruding Fibers (Hairy Disc)

A. Preparation of the center core

Clean the mold thoroughly, then apply an even coating of release agent; MR-1000 for Monothane products, then dry at 135 degrees C for 20 minutes. MR-5002 for Conathane then dry at 60 degrees C for five minutes.

Pour the deaired polyurethane or silicone into the metal disc-shaped core mold. Deair if needed and cure as before. For Ethicon Biomer pour only 2 mm coating at a time. The mold has a height of about 15 mm. The height of the core is about 7 mm.

B. Assembly of Spacer

Coat a thin layer of fresh liquid phase polyurethane or silicone on one side of the lamina. Wrap the freshly coated lamina around the cured polyurethane or silicone core. Tighten the spacer with back support in the posterior region and cure it as before. Remove the tape from the +45/−45 laminae's fiber end.

C. Attachment of the Endplate

1. Metal Endplate
   Coat the protruding fibers and endplates by using prepared epoxy with fibers pointing toward the periphery. The coating should be about 0.5 mm thick. Attach the spacer to the endplates and allow 30 minutes to cure. Apply force - approximately 10N - on top of the disc.

2. Polyurethane Endplate
   Place the protruding fiber spacer in hot water and thoroughly soak it. Arrange all the fibers towards the center or towards the periphery. Dry the arranged fibers face down on a flat surface in an oven at 90 degrees C for 20 minutes. Pour freshly deaired polyurethane liquid into the aluminum mold. Place one end of the spacer into the mold, cure in a nitrogen filled oven at a 50 degrees C for 1 hour. Form the other side of the polyurethane endplate as before and then cure at 80 degrees C for four hours. Continue to cure at room temperature for another 16 hours.

EXAMPLE 3

Formation of a Spacer Without Protruding Fibers

A. Preparation of the Core

Pour a thin layer of resin onto a 7 mm o/45/−45 degrees lamina. Wrap desired length around plastic core in between pins. The pins act as guides to keep the laminate layers at a constant 7 mm thickness. Once the wrap is completed, thread the back support screws upward until the laminate conforms to the plastic core shape. Cure the lamina with jig in the oven at 135 degrees C for one and one-half hours. Remove the jig from the oven, remove the press pins, and slide the annular laminae off the care. In a cavity mold, pour preheated resin on top of laminated core to fill up any voids and to flush the end surfaces. Cure as above.

B. Formation of the End Plates

1. Without Hydroxyapatite (HA)
   Preheat the disc mold (treated with release agent as detailed in Example 2) at 135 degrees C for 20 minutes. Inject hard grade resin into the mold up to a desired height; 2 ml without HA, 1 ml with hydroxyapatite. Cure in the oven at 135 degrees C. Check after 20 minutes to make sure that all entrapped air bubbles have escaped from the resin. Place procured laminate core into the disc mold with smooth surface down. Cure at 135 degrees C for one hour and 45 minutes. Preheat 10 mls of the soft grade polyurethane resin at 70 degrees C and inject over the hard grade resin to form the center core and outermost region. Cure the soft grade resin at 135 degrees C for 45 minutes. Inject 1 ml of endplate resin on top of semifinished spacer and cure for 4 hours. Inject another 1 ml resin on top of cured endplate and further cure for one hours.

2. With Hydroxyapatite
   Remove the semi-cured endplate disc from the mold and press in a layer of hydroxyapatite, then cure for two and one-half hours. Put spacer back into mold with the hydroxyapatite side down. Pour 1 ml of a hard grade resin on the top of the already cured endplate and cure for ninety minutes. Press the layer of hydroxyapatite and cure for an additional two and one half hours.

EXAMPLE 4

Mechanical Testing

MATERIAL PROPERTIES OF UNREINFORCED SILICONE AND POLYURETHANE ELASTOMERS

A series of spacers constructed from unreinforced elastomers were mechanically tested to compare their properties with those of natural discs.

The results are shown in Table 1.

TABLE 1

| SAMPLE | DESCRIPTION | E |
|---|---|---|
| | (Compressive Modulus (E) in Mpa) | |
| #4 | Natural Disc | 13.0 ± 1.90 |
| #13 | Natural Disc | 14.46 ± 4.30 |
| #15A | Natural Disc | 12.32 ± 2.14 |
| #10 | Degenerated Disc | 6.29 ± 1.01 |
| Silicone | MDX 4-4210 | 1.01 |
| Conathane | TV-400 | 2.68 |
| Biomer | — | 4.1 |
| Monothane | A40 | 2.016 |
| Monothane | A50 | 4.5 |
| Monothane | A70 | 14.91 |
| Monothane | A100 | 23 |
| Monothane | D65 | 52 |

REINFORCED SPACER PROPERTIES:

A total 161 spacers were made. The properties obtained from the mechanical tests are shown in FIGS. 6 to 11. The mechanical behavior of cadaver lumbar spine L4-5 motion segments are also included in these figures for comparison.

1. Silicone-Dacron Composite:

Twenty-four disc-shaped disc spacers were made of silicone-dacron composite. Fourteen spacers were manufactured with 45/−45 silicone-fiber laminae, and eight spacers were manufactured with 0/+45/−45 silicone-fiber laminae. The 0/+45/−45 spacers have nine layers of 0/+45/−45 laminae and were wrapped in such a way that 4 layers were clockwise and the remaining 5 layers were counterclockwise. FIG. 6 shows the results of the silicone-dacron composite compression tests, and FIG. 7 shows the torsion behavior under an 800N axial compression load. The compressive modulus ranges from 5 to 9.5 MPa. The mechanical properties of a spacer changes dramatically with the orientation of fibers, number of fibers in each orientation and the order of orientation. For example, from the spacer manufactured with +45/−45 lamina, it was determined that the mechanical properties did not increase significantly when the number of layers increased from five to six. But when the 0/+45/−45 lamina was used, a significant increase in the compressive and torsional stiffness was obtained when the number of layers increased from 7 to 9.

The uniaxial compression test and combined compression torsional test indicated that a [3(0),4(45/−45),2(0)] silicone-dacron spacer provided the natural disc property in compression, but did not provide the satisfactory torsional results.

A unidirectional spiral wrapping provided high torsional stiffness in the wrapping direction but lower stiffness in the opposite direction. For compression there was no change.

In addition to the static axial compression testing and compression-torsion testing, five spacers were tested in long-term fatigue tests. The spacers were tested in simultaneous compression and torsion fatigue. All of the fatigue tests were under an axial compression load control. The compression load cycled between 200 N and 800 N. The [3(0),10(4)] spacer was tested under axial load control and angular displacement control at a frequency of 3 Hz. The angular displacement was controlled at ±2.5 degrees. This fatigue test was terminated after one million cycles with no change in mechanical response. The [3(0),6(+45/−45)2(0)] spacer was tested under axial load control and torque control at the same frequency. The torque was set at ±2NM. This fatigue test was terminated at one million cycles with no reduction in axial and torsional response. Two prostheses with nine layers of 0/45/−45 laminae were tested in combined compression-torsion fatigue at ±3NM, 500 ±200N and 3 Hz. Due to the slippage between the aluminum endplate and the PMMA in the holding cup, one test was terminated at 720,000 cycles. Tee other one was terminated after one million cycles with no reduction in either axial displacement or angular rotation. I the last fatigue test, the spacer was the Biomer® fiber (0/45/−45) lamina disc with high modulus polyurethane end plate. The controllers were set at ±3 NM, 500±200N and 4 Hz frequency. The disc spacer survived more than one million cycles.

2. Biomer®-Dacron Composite:

One spacer was made of nine layers of 0/+45/−45 Ethicon Biomer-Fiber laminae with an aluminum endplate, and another was made to twelve layers of 0/45/−45 biomer laminae with a Conathane DPEN8488 polyurethane endplate. FIGS. 10 and 11 show the results of the former composite. The compressive modulus of the former was 17 MPa compared to the later one of 8.5 MPa.

The nine layered Biomer®-Dacron 0/+45/−45 spacer with aluminum endplates provided a superior compression stiffness an torsional stiffness.

The mechanical properties of the twelve layered Biomer®-Dacron spacer with high modulus polyurethane end plates are within the range of the natural discs. The lower stiffness of a twelve layer spacer as compared to those mentioned above is due to the lower compressive modulus of polyurethane endplates (125 MPa) as compared to higher modulus aluminum endplates (21000 MPa) in a nine-layer spacer.

3. Conathane® Spacer:

A total of thirty-six spacers were made of Conathane®. Ten spacers were made of Conathane® only, nine spacers were TU-DPEN sandwich disc, four spacers had four layers of +45/−45 laminae with DPEN endplates, and six spacers had six layers of +45/−45 laminae. The results of the mechanical tests showed that the composite had low compressive modulus ranging from 4 to 7 MPa.

4. Monathane® Spacer:

A total of fifty seven Monothane® polyurethane spacers were made using a combination of Monothane® A40 or A70 as the soft matrix and Monothane® and A100 or D65 as the endplate. The compression test results are presented as load-strain curves in FIG. 8. The compression-torsion test results are shown as applied torque versus angle of twit per unit length in FIG. 9. The compressive modulus of the A100-A40 composite ranges from 3.5 to 6 MPa, D65-A40 ranges from 9 to 17 MPa, and A100-A70 ranges from 30 to 50 MPa.

5. Summary

FIGS. 10 and 11 are the results of compression tests and compression-torsion tests n three different composites (Silicone, Biomer®, and Monothane®) with a comparison to natural discs. The functional specifications of the natural disc can be achieved by manufacturing a spacer with appropriate number of fibers, the orientation and their order. It can be seen from these figures that the compressive properties as well as the torsional properties of normal lumbar spine discs have been achieved by disc spacers of this invention. The mechanical functional behavior of an intervertebral joint can be reproduced by these spacers.

What is claimed is:

1. A biocompatible intervertebral spacer comprising:
   a central core having upper, lower and side surfaces and formed of a biocompatible elastomer shaped so as to approximate the nucleus pulposus of a natural intervertebral disc.
   A layered structure wrapped around the side surfaces, wherein said layered structure comprises between 3-24 separated laminae.
   and each of said lamina comprised of strips of biocompatible elastomer having unidirectional reinforcing fiber embedded therein;
   said fiber of each lamina having specific orientation;
   said laminae being bound together by biocompatible elastomer; and wrapped to sufficient thicknesses so as to approximate the shape of a natural intervertebral disc;
   and endplates comprised of a suitably stiff biocompatible material and affixed, one to each end, to the laminae/central core.

2. A spacer according to claim 1 wherein the biocompatible elastomer utilized is a thermoset polyurethane elastomer.

3. A spacer according to claim 1 wherein the biocompatible elastomer utilized is a thermoplastic polyurethane elastomer.

4. A spacer according to claim 1 wherein the biocompatible elastomer utilized is the polyurethane elastomer Biomer®.

5. A spacer according to claim 1 wherein the laminae wrapping the central core possess protruding fibers.

6. A spacer according to claim 1 wherein the endplates contain hydroxyapatite.

7. A spacer according to claim 1 wherein at least one of said lamina having fibers oriented at 0 degrees and at least one of the other lamina having fibers oriented at 20-50 degrees said fiber orientation in each lamina being selected from the group consisting of 0 degrees and ±20-50 degrees.

8. A spacer according to claim 7 wherein the biocompatible elastomer utilized is a thermoset polyurethane elastomer.

9. A spacer according to claim 7 wherein the biocompatible elastomer utilized is a thermoplastic polyurethane elastomer.

10. A spacer according to claim 7 wherein the biocompatible elastomer utilized is the polyurethane elastomer Biomer®.

11. A spacer according to claim 7 wherein the laminae wrapping the central core possess protruding fibers.

12. A spacer according to claim 7 wherein the endplates contain hydroxyapatite.

13. A spacer according to claim 7 wherein the layered structure comprises 6-15 laminae.

14. A spacer according to claim 13 wherein the biocompatible elastomer utilized is a thermoset polyurethane elastomer.

15. A spacer according to claim 13 wherein the biocompatible elastomer utilized is a thermoplastic polyurethane elastomer.

16. A spacer according to claim 13 wherein the biocompatible elastomer utilized is the polyurethane elastomer Biomer®.

17. A spacer according to claim 13 wherein the laminae wrapping the central core possess protruding fibers.

18. A spacer according to claim 13 wherein the endplates contain hydroxyapatite.

19. A spacer according to claim 1 wherein the layered structure comprises 6-15 laminae and at least one of said lamina having fibers oriented at 0 degrees and at least one of the other lamina having fibers oriented at 45 degrees.

20. A spacer according to claim 19 wherein the biocompatible elastomer utilized is a thermoset polyurethane elastomer.

21. A spacer according to claim 19 wherein the biocompatible elastomer utilized is a thermoplastic polyurethane elastomer.

22. A spacer according t claim 19 wherein the biocompatible elastomer utilized is the polyurethane elastomer Biomer®.

23. A spacer according to claim 19 wherein the laminae wrapping the central core possess protruding fibers.

24. A spacer according to claim 19 wherein the endplates contain hydroxyapatite.

25. A spacer according to claim 1 wherein the endplates are metal.

26. A spacer according to claim 1 wherein the endplates have a porous sintered surface.

27. A spacer according to claim 1 sized so as to approximate the size of a natural disc.

28. A spacer according to claim 1 sized so as to approximate 30-80 % of the size of a natural disc.

29. A spacer according to claim 22 wherein the laminae are arranged in a layered structure and the fiber orientation of the laminae is in a pattern of −45/+45/0 degree.

* * * * *